United States Patent [19]
Calcote et al.

[11] Patent Number: 5,453,235
[45] Date of Patent: Sep. 26, 1995

[54] METHOD OF FORMING DUAL POROSITY PTFE TUBES BY EXTRUSION OF CONCENTRIC PREFORMS

[75] Inventors: Robert W. Calcote; Rajagopal R. Kowligi, both of Phoenix,, Ariz.; Stacy Wollner, Kewaskum, Wis.

[73] Assignee: Impra, Inc., Tempe, Ariz.

[21] Appl. No.: 10,974

[22] Filed: Jan. 29, 1993

[51] Int. Cl.$^6$ .......................... B29C 47/06; B29C 55/22
[52] U.S. Cl. .................. 264/127; 264/209.5; 264/288.8; 264/289.3
[58] Field of Search ................. 264/127, 288.8, 264/289.3, 41, 209.5

[56] References Cited

U.S. PATENT DOCUMENTS

| | | | |
|---|---|---|---|
| 3,833,455 | 9/1974 | Rosenblatt, Jr. et al. | 156/626 |
| 4,082,893 | 4/1978 | Okita | 428/376 |
| 4,110,392 | 8/1978 | Yamazaki | 264/127 |
| 4,187,390 | 2/1980 | Gore | 174/102 R |
| 4,208,745 | 6/1980 | Okita | 3/1.4 |
| 4,550,447 | 11/1985 | Seiler, Jr. et al. | 264/289.3 |
| 4,743,480 | 5/1988 | Campbell et al. | 264/288.8 |
| 4,816,339 | 3/1989 | Tu et al. | 428/421 |
| 4,822,361 | 4/1989 | Okita et al. | 623/12 |
| 4,877,661 | 10/1989 | House et al. | 264/288.8 |
| 4,882,113 | 11/1989 | Tu et al. | 264/127 |
| 4,973,609 | 11/1990 | Browne | 521/81 |
| 5,064,593 | 11/1991 | Tamaru et al. | 264/127 |
| 5,071,610 | 12/1991 | Hagen et al. | 264/127 |
| 5,102,921 | 4/1992 | Harada et al. | 264/127 |

FOREIGN PATENT DOCUMENTS 0113869 6/1984 European Pat. Off. ................ 264/127

OTHER PUBLICATIONS

"FLUON© PTFE Coagulated Dispersion Powders for Paste Extrusion—Summary of Properties", pp. 1–4, ICI Advanced Materials, Exton, Pa. 19341 (1989).

"The Processing of PTFE Coagulated Dispersion Powders", pp. 1–36, ICI Advanced Materials, Exton, Pa. 19341 (1989).

*Primary Examiner*—Allan R. Kuhns
*Attorney, Agent, or Firm*—David G. Rosenbaum; Laura J. Zeman

[57] ABSTRACT

A dual porosity PTFE tube including an inner surface of expanded PTFE material having a first porosity and an outer surface of expanded PTFE material having a porosity different from that of the inner surface. The preferred method includes the step of forming inner and outer preformed tubular billets of PTFE resin particles mixed with a lubricant; the outer billet is adapted to closely fit around and concentric to the inner billet. Porosity of the inner and outer surfaces is varied by changing, in the respective billets, the lubrication level and/or the PTFE resin characteristic average particle size. The inner billet is placed inside the outer billet, and the two are extruded together, thereby melding the two billets. The extrudate is then longitudinally expanded and sintered. The inner surface of the resulting PTFE tube exhibits a different porosity than the outer surface of the tube; the porosities of the inner and outer surfaces are both within a range of about 0.10–200μ.

5 Claims, 2 Drawing Sheets

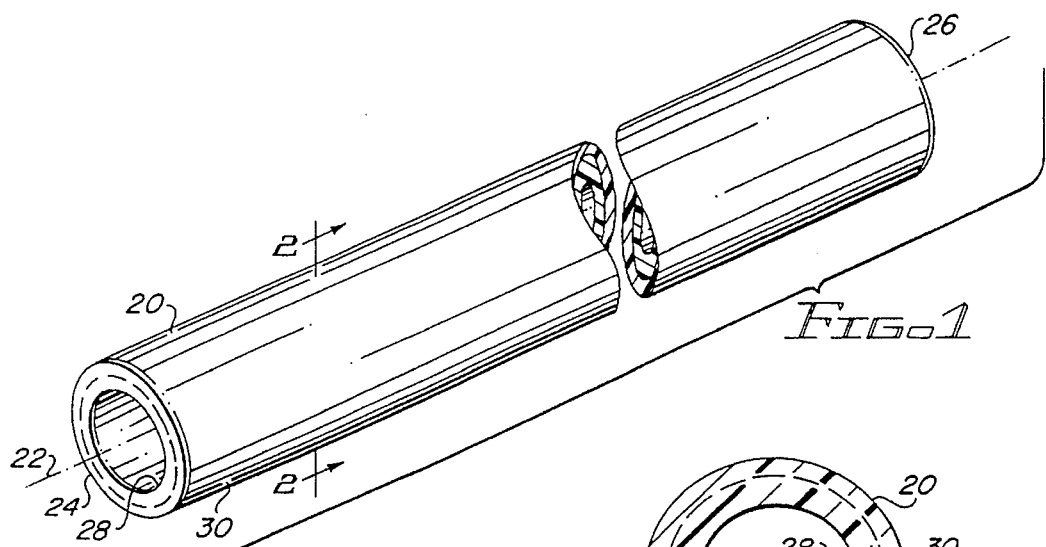
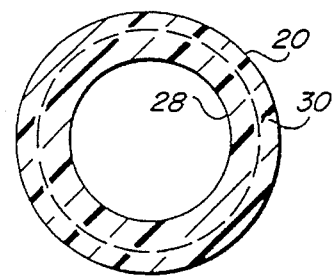
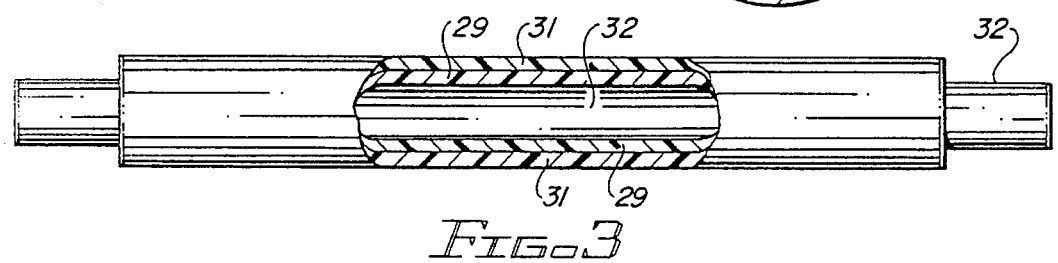
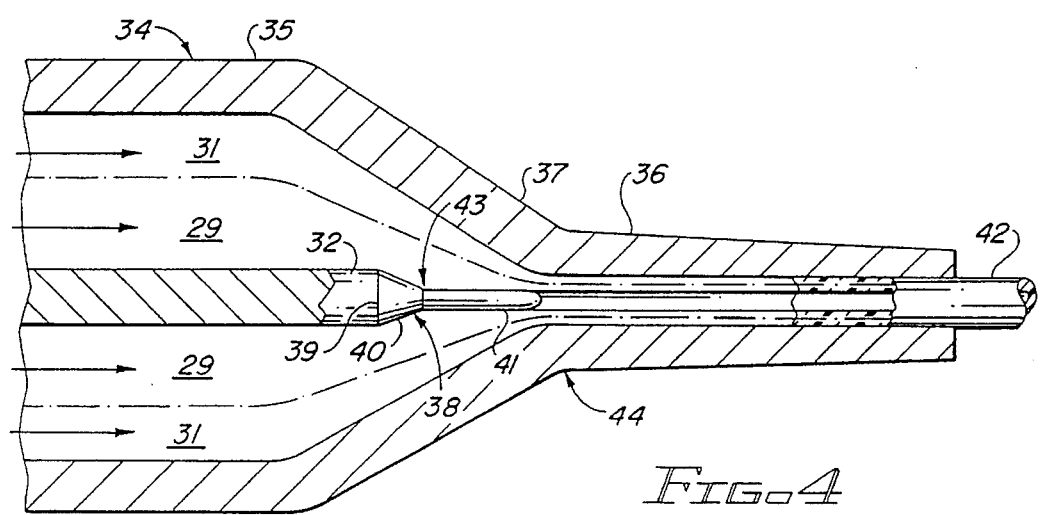

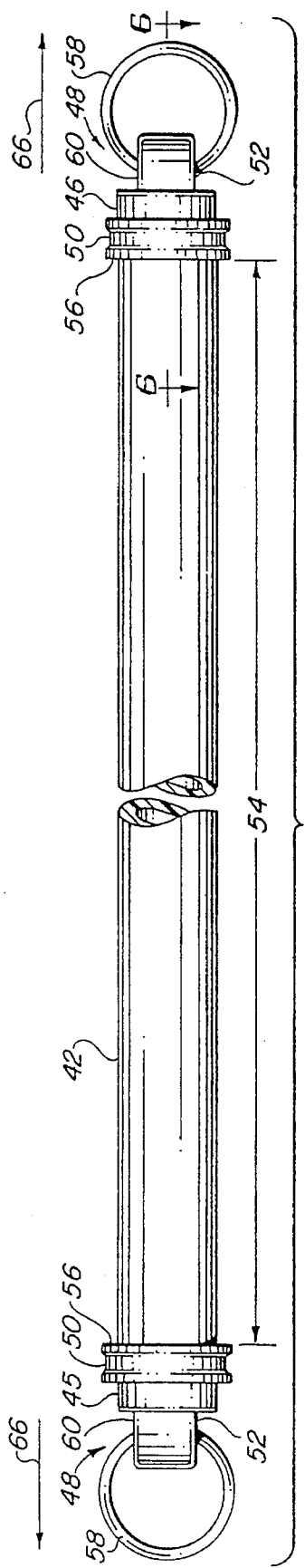
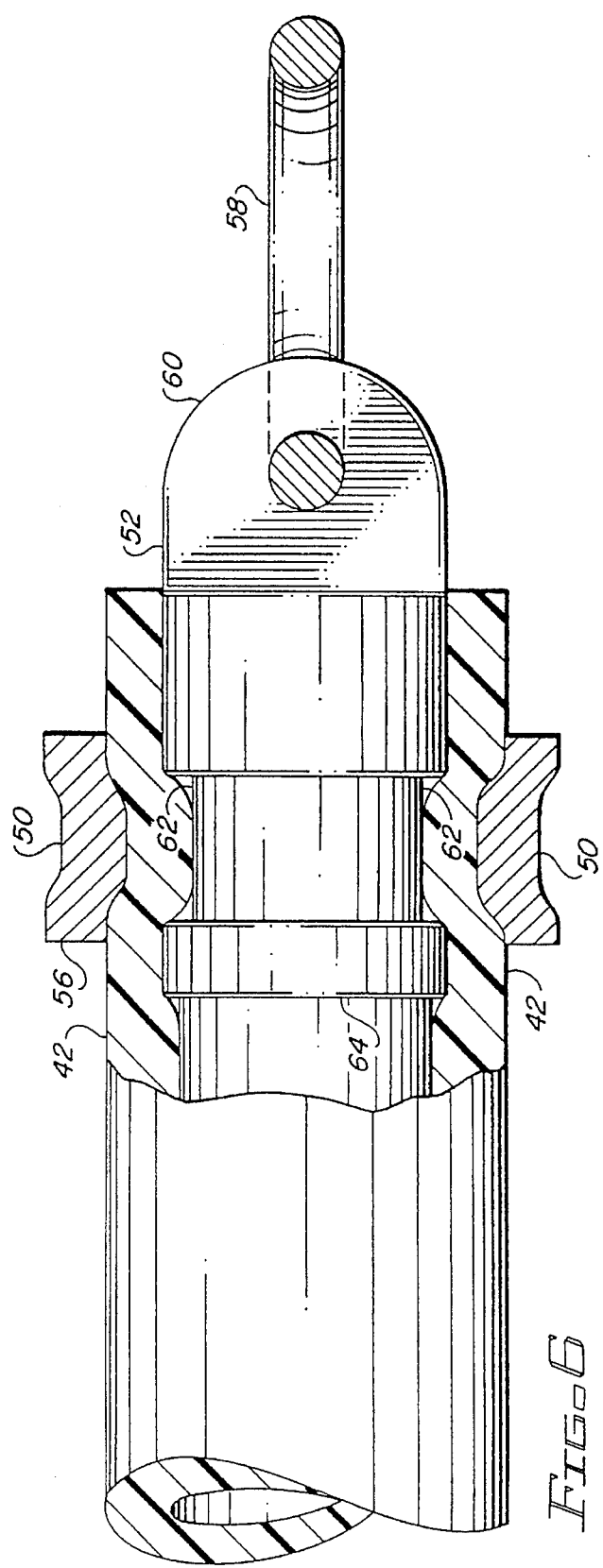

METHOD OF FORMING DUAL POROSITY PTFE TUBES BY EXTRUSION OF CONCENTRIC PREFORMS

FIELD OF THE INVENTION

This invention relates generally to dual porosity polytetrafluoroethylene (PTFE) tubes or prosthetic vascular grafts for implantation within the vascular system of a patient and, in addition, to a method for making a dual porosity PTFE tube or prosthetic vascular graft.

BACKGROUND OF THE INVENTION

The use of implantable prosthetic vascular grafts made of expanded, porous PTFE is well known in the art. Such vascular grafts are used to replace or bypass occluded or damaged natural blood vessels and are often implanted just below the skin to provide blood access for long term hemodialysis. Prosthetic vascular grafts, and methods of implanting the same, are generally described in Bennion et al., "Hemodialysis and Vascular Access", *Vascular Surgery*, pp. 625–662, 1983. Methods of forming expanded, porous PTFE tubing are well known in the art. For example, U.S. Pat. No. 4,187,390 issued to Gore discloses one such process of extruding, expanding, and then heating PTFE to produce porous, expanded PTFE structures, and the specification of such patent is hereby incorporated by reference.

In a typical technique, PTFE is provided in the form of a "coagulated dispersion" which is then extruded to a desired shape and then sintered, i.e., heated somewhat above its melting point for a time sufficient for it to coalesce into an essentially impermeable material, to produce the resulting product. A thorough discussion of PTFE coagulated dispersion powder properties and processing techniques is set forth in the technical data bulletin entitled "FLUON® PTFE COAGULATED DISPERSION POWDERS FOR PASTE EXTRUSION—SUMMARY OF PROPERTIES", pages 1–4, and in "The Processing of PTFE Coagulated Dispersion Powders", pages 1–36; both references, the contents of which are also entirely incorporated herein by reference, are available from ICI Advanced Materials, Exton, Pa. 19341.

As discussed in the references incorporated herein, PTFE coagulated dispersion ("CD") polymers are typically supplied as a fine, free flowing powder. These dispersions are manufactured by coagulating an aqueous dispersion of PTFE. In order to extrude such dispersions, the coagulated dispersion polymers are blended with an "extrusion aid" or lubricant. A typical lubricant is a hydrocarbon having a desired vaporization temperature; examples are petroleum ether, naphtha, and low odor paraffin solvents. A number of such solvents, and the reasons for selecting a particular solvent, are also discussed in the references incorporated above.

The dry-appearing mix of dispersion and lubricant is them lightly pressed into a billet or preform. Such preforms are stiff and brittle and similar in consistency to soft wax candles. The preform billet is them forced through the simple die of a constant rate ram extruder. The tubular extrudate typically passes into a drying oven, the temperature of which is sufficient to vaporize the lubricant.

PTFE can be stretched to many times its original dimensions. Prior to expansion, the PTFE tubular extrudate, or "tube", is typically heated to approximately within the range of 225–300 degrees Centigrade. Upon reaching such temperature, the tube is expanded by stretching to a desired dimension. Following expansion, the PTFE tube is heated to a higher sintering temperature of approximately 375 degrees Centigrade or higher to lock the crystalline structure to its expanded dimensions. During this sintering step, the expanded PTFE tube must be held to its expanded dimensions, or the tube will contract partially back toward its pre-expanded shape.

Expanded, porous PTFE material offers a number of advantages when used as a prosthetic vascular graft. PTFE is highly biocompatible, has excellent mechanical and handling characteristics, does not require preclotting with the patient's blood, heals relatively quickly following implantation, and is thromboresistant. In general, large pore size PTFE grafts enhance vascular graft patency because grafts with large interstitial spaces improve healing by increased tissue ingrowth. However, large porosity grafts have an increased tendency to bleed and cause seroma after the graft is implanted. Therefore, a balance must be struck between a large enough pore size for good tissue ingrowth, and a small enough pore size to prevent bleeding through the graft.

U.S. Pat. No. 4,082,893 to Okita describes a PTFE tube that is processed to produce a variation in the microporous structure as between the inner surface of the tubing and the outer surface of the tubing. For example, the tubing may have pores with a 10 micron diameter at the inner surface, and pores with a 3 micron diameter at the outer surface. Variation in the microporous structure as between the inner and outer surfaces is induced by heating the outer surface of the tube to a greater degree than the inner surface of the tube, as by heating the tube externally while passing cooling air through the inner cavity of the tube.

U.S. Pat. No. 4,208,745 to Okita discloses a PTFE vascular graft wherein the fibrous structure at the inside surface of the tubing is finer than the fibrous structure at the outside surface of the tubing; for example, the tubing may have a pore size on the outside surface of at least 3 microns, and a pore size os 1 to 5 microns on the inside surface. As in the '893 Okita patent, the variation in porosity between the inner and outer surfaces is created by heating the outer surface to the sintering temperature while maintaining the inner surface at a lower temperature.

U.S. Pat. No. 4,816,339 to Tu et al is directed to a multi-layered PTFE/elastomer composite graft wherein the various layers may have different pore sizes. The different porosities within the multiple layers are caused by radial expansion of such layers. The first and second PTFE layers are preformed and extruded together to form separate layers. The resulting extrudate is expanded biaxially or uniaxially. The resulting structure is then sintered. In the preforming stage, a concentric tube is inserted inside the pre-former to divide the pre-former into two concentric spaces. The inner space is loaded with pure PTFE, while the outer space is loaded with a PTFE/elastomer mixture. Following extrusion, the extrudate is expanded and sintered. The inner layer internodal distance is described as being about 20 to 30 microns, in comparison to the second layer internodal distance, which is described as being in the range of between 30 to 500 microns.

U.S. Pat. No. 4,822,361 to Okita et al. discloses a PTFE tubular prosthesis formed from a single PTFE tube rather than from two concentric tubes. The prosthesis has a greater average fibril length on its outer surface than on its inner surface, and the fibril length is described as varying continuously across the wall of the tube. The outer surface of the tube has a larger average pore size than the inner surface of the tube; the outer surface pore size is apparently in the range of 1 to 100 microns, while the inner surface pore size is apparently in the range of from 0.1 to 1 microns. The variance in porosity from the inner surface to the outer surface is evidently accomplished by radial inflation of the tube.

Accordingly, it is an object of the present invention to provide a dual porosity PTFE tube or graft and method for making same, which tube or graft includes an inner surface of expanded PTFE having a porosity in the range of about 10–40μ, to reduce blood leakage, and an outer surface having a porosity in the range of about 60–155μ, to enhance tissue ingrowth.

It is another object of the present invention to provide a dual porosity PTFE tube or graft and method for making same, which tube or graft includes an inner surface of expanded PTFE having a porosity in the range of about 60–155μ, and an outer surface having a porosity in the range of about 10–40μ, to accelerate healing of an implanted vascular graft.

These and other objects of the present invention will become more apparent to those skilled in the art as the description thereof proceeds.

SUMMARY OF THE INVENTION

Briefly described, and in accordance with a preferred embodiment thereof, the present invention relates to a dual porosity PTFE tube including an inner surface of expanded PTFE material in tubular form having a first porosity, and an outer surface of expanded PTFE material in tubular form having a porosity different from that of the first surface. The porosity of the inner surface and the porosity of the outer surface are both within a range of about 0.1–200μ.

The preferred method of making a dual porosity PTFE tube includes the step of forming an inner preformed tubular billet and an outer preformed tubular billet; the outer billet is adapted to closely fit concentrically within the inner billet. Porosity of the inner and outer surfaces is varied within a range of about 0.1–150μ by changing, in the respective billets, the lubrication level and/or PTFE resin particle size. The inner billet is placed inside the outer billet and the two are extruded together, thereby merging the two billets into a composite whole. The extrudate is dried and then longitudinally expanded and sintered. The inner surface of the resulting PTFE tube exhibits a porosity different from that of the outer surface of the tube. In a first embodiment, the inner surface is made less porous to reduce blood leakage, while the outer surface is made more porous to enhance tissue ingrowth. In a second embodiment, the aforementioned porosity is reversed, that is, the inner surface is made more porous while the outer surface is made less porous, to accelerate healing of an implanted vascular graft.

BRIEF DESCRIPTION OF THE DRAWINGS

FIG. 1 is a perspective view of a dual porosity PTFE tube or vascular graft made in accordance with the teachings of the present invention.

FIG. 2 is a cross-sectional drawing of the tube shown in FIG. 1 taken through the lines designated 2—2 within FIG. 1, to demonstrate the merging of the inner and outer billets.

FIG. 3 is a top view of concentrically aligned inner and outer billets pulled onto a supporting shaft prior to extrusion.

FIG. 4 is a perspective view of an extrusion die for extruding concentrically aligned inner and outer billets.

FIG. 5 is a perspective view of crimping apparatus adapted to secure the opposing ends of the extrudate and aid in its longitudinal expansion.

FIG. 6 is a cross-sectional drawing of the crimping apparatus shown in FIG. 5 taken through the lines designated 6—6 within FIG. 5, to demonstrate in detail crimping of the extrudate.

DETAILED DESCRIPTION OF THE PREFERRED EMBODIMENTS

In FIG. 1, a dual porosity PTFE tube or vascular graft made in accordance with the teachings of the present invention is designated generally by reference numeral 20. As shown, vascular graft 20 is tubular and can have any desired length, internal diameter, and wall thickness. Within FIG. 1, dashed line 22 indicates the central longitudinal axis of vascular graft 20. Vascular graft 20 includes first end 24 and opposing second end 26.

Vascular graft 20 includes inner surface 28 of expanded PTFE material having a first porosity, and outer surface 30 of expanded PTFE material having a second porosity different from that of inner surface 28. The preferred starting material used to form graft 20 is PTFE resin such as that commercially available from DuPont, or, preferably, the PTFE resin FLUON® available from ICI Advanced Materials, Exton, Pa. 19341.

Both inner surface 28 and outer surface 30 are characterized by nodes interconnected by fibrils. Inner and outer surface porosity is measured by the internodal distance, or IND, of each respective surface; the higher the IND, the higher the porosity. In a first embodiment of a tubular vascular graft made by the invention, the IND of inner surface 28 is less than about 40 micrometers or microns ("μ"), preferably in the range of about 10 to 40μ, while the IND of outer surface 30 is greater than 55μ, preferably in the range of about 60μ to 150μ. In a second embodiment, the porosity is reversed, that is, the IND of inner surface 28 is greater than 55μ, preferably in the range of about 60μ to 150μ, while the IND of outer surface 30 is less than about 40μ, preferably in the range of about 10μ to 40μ; such reversed-porosity grafts are useful in clinical applications where it is expected that healing will occur faster when the inner surface of a graft has a high porosity rather than a low porosity.

In practicing the preferred method, the initial step is forming inner and outer separately preformed tubular PTFE billets 29 and 31, respectively. To form each billet, as described in the ICI Advanced Materials references incorporated earlier herein, unsintered PTFE resin particles are uniformly mixed with an extrusion aid or lubricant such as mineral spirits, naphtha or equivalent volatile petroleum derivatives; the mixtures are placed in respective metal tubes (not shown) and preformed by compression in the tubes to form the respective billets.

PTFE tubing porosity or pore size, as measured by IND, is dependent on various processing parameters such as lubrication level and PTFE average resin particle size. It has been discovered that the porosity of PTFE tubing increases with an increase in PTFE resin particle size and/or with an increase in the amount of lubricant. Therefore, a difference in porosity, within a range of about 10–150μ, between inner and outer surfaces 28 and 30 is accomplished by varying the average particle size of the PTFE resin in inner and outer billets 29 and 31 within a range of about 100–900μ, and/or by varying the amount of lubricant within a range of about 50–150 grams of lubricant per 500 grams of PTFE resin. The amount of lubricant, in grams, per 500 grams of PTFE resin is referred to as the "lube level"; e.g., a paste having 100 grams of lubricant and 500 grams of PTFE is referred to as "100 lube level paste".

To form a low porosity surface, PTFE resin having a characteristic particle size less than 200μ can be used to form the corresponding billet; to form a surface having a comparatively high porosity, PTFE resin having a characteristic particle size of more than 700μ can be used to form the corresponding billet. For example, in a first preferred embodiment, inner surface 28 has a low porosity while outer surface 30 has a comparatively high porosity. Such a result can be achieved by forming inner billet 29 from PTFE resin having an average PTFE resin particle size of less than about 200μ, and forming inner billet 31 from PTFE resin having an average particle size of more than 700μ. Particles having the appropriate size can be obtained by sifting the resin particles through appropriately-sized mesh screens. Alternatively, the porosity of inner and outer surfaces 28 and 30 can be varied by holding the average particle size constant and changing the lube level in the respective inner and outer billets 29 and 31. For example, 80 lube level paste can be used to form an inner billet which will result in a low porosity inner surface, and 120 lube level paste can be used to form an outer billet resulting in a comparatively high porosity outer surface.

After the PTFE resin and lubricant are mixed and preformed in separate metal tubes to create billets 29 and 31, each billet is removed from its respective metal tube. Inner billet 29 is then inserted concentrically into outer billet 31 so that the inner billet snugly fits within the outer billet. As shown in FIG. 3, concentrically aligned billets 29 and 31 are pulled over cylindrical supporting shaft 32 which has an outer diameter that is equal to or slightly smaller than the internal diameter of inner billet 29.

FIG. 4 illustrates an extrusion die 34 for melding separate billets 29 and 31, aligned concentrically on shaft 32, into a tube with the result that, as shown in FIG. 2, the original, separate billets are inseparable and visually indistinguishable; after extrusion, visual distinctions between the two billets used to form the tube can be seen only by mixing a dye into one of the two billets prior to extrusion. Specifically, die 34 includes large diameter portion 35 and small diameter portion 36 connected by tapered portion 37. Inside die 34, a mandrel 38 is attached to first end 39 of shaft 32 by a screw or other suitable means (not shown); the mandrel includes a tapered portion 40 and a small diameter portion 41. Mandrel 38 can move longitudinally within die 34 to locate tapered portion 40 closer to or further away from the junction between die tapered portion 37 and die small diameter portion 36. This change in position of mandrel 38 changes the amount of compression applied to the concentrically aligned billets as they are merged and forced out of the die as tubular extrudate 42.

In operation, shaft-supported concentrically aligned billets 29 and 31 are loaded into a ram extruder (not shown) attached to die 34, and the billets are forced through die 34, thereby merging or melding the two billets into extrudate 42. Several parameters must be controlled in operating the die. These include, but are not limited to, mandrel placement, extrusion speed, and mandrel temperature.

In its preferred or "normal" position, the outer end of mandrel tapered portion 40 is located at the position indicated by arrow 43, separated approximately 0.5 inches from the junction of die tapered portion 37 with small diameter portion 36. This provides a relatively wide passageway for the billets as they are constricted moving through die tapered portion 37. When mandrel 38 is moved forward, i.e., advancing the outer end of mandrel tapered portion 40 to the position indicated by arrow 44, the passageway for the billets is substantially narrowed, increasing the local pressure on the billets and more completely merging them.

Extrusion speed can be varied in the range of about 3–6 inches extrudate per second to control the melding of the two billets. In some circumstances, e.g., when the mandrel is moved forward, it is preferred to reduce extrusion speed to about 1–2 inches per second. In addition, the mandrel may be unheated, or may be heated to a temperature in the range of about 25°–200° C. during extrusion.

It has been discovered that the extrusion parameters described above affect the properties of the final graft. For example, a forward-positioned mandrel and a slower speed will result in a decrease in the IND of outer surface 30. Heating the mandrel during extrusion also decreases IND of outer surface 30. If the mandrel is moved forward and heated and if the extrusion speed is reduced, the decrease of IND in the outer surface is compounded.

In FIG. 5, opposing ends 45 and 46 of extrudate 42 are secured by a pair of crimping tools 48; the crimping tools are part of apparatus sued to expand or stretch the extrudate various amounts at controlled rates and temperatures, as described in the U.S. Patent to Gore incorporated earlier herein. Crimping tools 48 each include metal band 50, adapted to closely circumscribe extrudate 42 and plug 52, adapted to fit tightly within opposing ends 45 and 46 of the extrudate. Arrow 54 illustrates the tie length (or distance between opposing inner ends 56 of band 50) of extrudate 42. The tie length is the length of extrudate 42 which is expanded and used as a dual porosity tube or graft; the crimped ends of the extrudate are waste. Each plug 52 includes a hook 58 positioned in its respective outer end 60, and also has a shallow annular cutout section 62 which defines plug outer end 60 and plug inner end 64; preferably, the plug outer end is longer than the plug inner end. As shown in detail in FIG. 6, to secure opposing ends 45 and 46 of extrudate 42, bands 50 are pressed or "crimped" inwardly into cutout section 62 by a suitable crimper (not shown), such as a wire crimper (commercially available from tool manufacturers such as Sears Roebuck), thereby forcing into the cutout section that portion of extrudate 42 which is adjacent the cutout section.

Crimped extrudate 42 is then dried in an oven to evaporate the lubricant. After drying, crimped extrudate 42 is heated to approximately within the range of 225°–300° C. and then longitudinally expanded by stretching to a desired dimension.

Extrudate 42 is expanded at a rate in the range of about 5% per second to 10% per second by pulling hooks 58 in opposite directions, indicated by arrows 66, until a predetermined expansion ratio (representing the ratio of expanded length to original tie length) is achieved. Preferred expansion ratios range from about 6.3:1 to about 2.5:1. The expanded extrudate is then sintered; after sintering, the graft is cooled and then cut away from crimping tools 48 at the positions adjacent to opposing inner ends 56 of bands 50.

The following examples describe the preparation of several PTFE grafts having inner and outer surfaces of different porosities, and are meant to be purely illustrative and nonlimiting.

EXAMPLE 1

An inner PTFE billet was formed in a metal tube by uniformly mixing unsintered PTFE resin particles having a characteristic average particle size of less than 355μ with mineral spirits at a lube level of 80. The inner billet outer diameter, or OD, was 1.25 inches; the inner billet inner diameter, or ID, was 0.5 inches.

An outer PTFE billet was formed in a metal tube by uniformly mixing unsintered PTFE resin particles having a characteristic average particle size of 450μ with mineral spirits at a lube level of 120. The outer billet OD was 2.00 inches; the outer billet ID was 1.26 inches.

Both the inner and outer billets were then preformed and then removed from each respective metal tube. The inner billet was then slid through the outer billet so that the outer billet fit snugly concentric to the inner billet.

The concentrically aligned inner and outer billets were then pulled over a cylindrical supporting shaft which had an OD of 0.50 inches. The shaft-supported billets were then loaded into a ram extruder, the shaft was attached to a mandrel, and several 6 millimeter tubes or grafts were extruded through a die at an extrusion pressure of 1150 psi and extrusion speed of 5.67 inches per second. During extrusion, the mandrel was in the normal position, about 0.5 inches from the end of the die, and was not heated.

The extrudate was used to prepare four grafts crimped at tie lengths of 8, 10, 12, and 14 inches, respectively, using a 6 Straight tooling plug. The crimped grafts were dried at 40° C. for one hour, incubated for five minutes, and then longitudinally expanded to 38 inches (corresponding to respective expansion ratios of 4.8:1, 3.8:1, 3.2:1, and 2.7:1) at a rate of 10% per second in an oven having an air temperature ("$T_A$") of 275° C. The expanded extrudate was then sintered in an oven having a $T_A$ of 380° C. Following sintering, the grafts were cooled and then cut from the crimping apparatus. Porosity measurements of the inner and outer surfaces of the grafts resulting from Example 1 are set forth below in Table 1.

TABLE 1

| Graft Tie Length | Inner Surf. IND, avg | Outer Surf. IND, avg |
| --- | --- | --- |
| 8 inches | 24 μ | 68 μ |
| 10 inches | 20 μ | 60 μ |
| 12 inches | 12 μ | 52 μ |
| 14 inches | 12 μ | 40 μ |

EXAMPLE 2

Inner and outer PTFE billets were prepared as described above in Example 1, except that the extrusion conditions were changed as follows. The mandrel was placed in a forward position (that is, even with the end of the die) and extrusion occurred at a slower speed, 1.8 inches per second. As in Example 1, the extrudate was used to prepare four grafts crimped at tie lengths of 8, 10, 12, and 14 inches, respectively, using a 6 straight tooling plug, and expanded and sintered as described in Example 1. Porosity measurements of the inner and outer surfaces of the grafts resulting from Example 2 are set forth below in Table 2.

TABLE 2

| Graft Tie Length | Inner Surf. IND, avg | Outer Surf. IND, avg |
| --- | --- | --- |
| 8 inches | 32 μ | 48 μ |
| 10 inches | 20 μ | 35 μ |
| 12 inches | 20 μ | 36 μ |
| 14 inches | 12 μ | 32 μ |

EXAMPLE 3

Inner and outer PTFE billets were prepared as described above in Example 1, except that the extrusion conditions were changed as follows. The mandrel was heated to a temperature of 119° C. and extrusion occurred at a speed of 3.8 inches per second. As in Example 1, the extrudate was used to prepare four grafts crimped at tie lengths of 8, 10, 12, and 14 inches, respectively, using a 6 straight tooling plug, and expanded and sintered as described in Example 1. Porosity measurements of the inner and outer surfaces of the grafts resulting from Example 3 are set forth below in Table 3.

TABLE 3

| Graft Tie Length | Inner Surf. IND, avg | Outer Surf. IND, avg |
| --- | --- | --- |
| 8 inches | 24 μ | 48 μ |
| 10 inches | 12 μ | 40 μ |
| 12 inches | 8 μ | 32 μ |
| 14 inches | 8 μ | 24 μ |

EXAMPLE 4

Inner and outer PTFE billets were prepared as described above in Example 1, except that the extrusion conditions were changed as follows. The mandrel was placed in a forward position (that is, even with the end of the die), extrusion occurred at a slower speed, 1.8 inches per second, and the mandrel was heated to a temperature of 190° C. As in Example 1, the extrudate was used to prepare four grafts crimped at tie lengths of 8, 10, 12, and 14 inches, respectively, using a 6 straight tooling plug, and expanded and sintered as described in Example 1. Porosity measurements of the inner and outer surfaces of the grafts resulting from Example 4 are set forth below in Table 4.

TABLE 4

| Graft Tie Length | Inner Surf. IND, avg | Outer Surf. IND, avg |
| --- | --- | --- |
| 8 inches | 16 μ | 28 μ |
| 10 inches | 12 μ | 24 μ |
| 12 inches | 8 μ | 24 μ |
| 14 inches | 8 μ | 16 μ |

A laboratory simulation was used to determine suture retention strength of dual porosity PTFE vascular grafts produced in accord with the four Examples. Suture retention strength is an indication of the ability of the graft to resist shearing or breaking when a suture or a pin is forced through the material and pulled in a direction perpendicular to the entry direction. This strength is measured by piercing a 0.012 inch needle (attached to a calibrated force gage) through one wall of the graft at a point (designated the "bite size") 2 mm from the end of the graft. The graft sample is then pulled away from the force gage at a constant speed until it breaks at the puncture site. The peak force recorded on the force gage is the suture retention strength. The results of the suture retention strength test are set forth in Table 5 below.

The aforementioned laboratory simulation also included an investigation of the water entry pressure ("WEP") for the dual porosity PTFE grafts described above. Water entry pressure is a test of the pressure at which water applied to the inner passageway of the graft leaks through the outer porous wall of the PTFE tube, and thereby serves as a measure of the tendency for such a vascular graft to exhibit serous weepage when implanted in the body. The water entry pressures noted for the grafts described above are also set forth Table 5, below, and show that the dual porosity PTFE tube has water entry pressure values that are higher than the normal systemic blood pressures, which lessens the tendency of the graft to exhibit serous weepage, even at high porosities.

TABLE 5

| TL (inches) | WEP (psi) | Suture Retention Strength (kg) |
| --- | --- | --- |
| EXAMPLE 1 -- GRAFTS | | |
| 8 | 3.4 | 0.877 |
| 10 | 4.0 | 1.172 |
| 12 | 5.3 | 1.452 |
| 14 | 6.2 | 1.616 |
| EXAMPLE 2 -- GRAFTS | | |
| 8 | 3.2 | 0.846 |
| 10 | 4.2 | 1.211 |
| 12 | 5.1 | 1.315 |
| 14 | 6.3 | 1.738 |
| EXAMPLE 3 - GRAFTS | | |
| 8 | 5.6 | 0.793 |
| 10 | 6.6 | 1.297 |
| 12 | 8.8 | 1.276 |
| 14 | 11.4 | 1.682 |
| EXAMPLE 4 - GRAFTS | | |
| 8 | 6.0 | 0.667 |
| 10 | 6.8 | 1.198 |
| 12 | 8.8 | 1.386 |
| 14 | 11.0 | 1.820 |

EXAMPLE 5

Inner and outer PTFE billets were prepared under conditions as described above in Example 1, with the following changes.

Both inner and outer billets had a lube level of 80. The inner billet was formed from PTFE resin having a characteristic average particle size of less than 200μ; the outer billet was formed from PTFE resin having a characteristic average particle size of greater than 700μ.

The resulting extrudate was used to prepare several grafts crimped at a tie length of 7 inches, dried, expanded to 38 inches (corresponding to an expansion ratio of 5.5:1), and sintered. Porosity measurements of the inner and outer surfaces of the grafts resulting from Example 5 are as follows:

Inner surface porosity: 24μ
Outer surface porosity: 56μ

EXAMPLE 6

Two groups of inner and outer PTFE billets were produced. In Group One, the inner billet had a low lube level while the outer billet had a high lube level. In Group Two, the inner billet had a high lube level while the outer billet had a low lube level. In other words, Group Two represents the reverse of Group One. Both sets of billets were prepared under conditions as described above in Example 1, with the following changes.

Group One: The inner billet was formed from PTFE resin having a characteristic average particle size of 450μ and had a lube level of 70. The outer billet was formed from PTFE resin having a characteristic average particle size of 450μ and had a lube level of 130.

Group Two: The inner billet was formed from PTFE resin having a characteristic average particle size of 450μ and had a lube level of 130. The outer billet was formed from PTFE resin having a characteristic average particle size of 450μ and had a lube level of 70.

The extrudate of each group was used to prepare several grafts crimped at a tie length of 7 inches, dried, expanded to 38 inches (corresponding to an expansion ratio of 5.5:1), and sintered. Porosity measurements of the inner and outer surfaces of the grafts resulting from Example 6 are as follows:

Group One: Inner surface porosity: 20μ Outer surface porosity: 60μ

Group Two: Inner surface porosity: 60μ
Outer surface porosity: 20μ

Those skilled in the art will now appreciate that an improved dual porosity PTFE tube has been described which may be used wherever prosthetic vascular grafts are currently used today, including both peripheral vascular applications and vascular access applications. The above-described graft may be implanted in the same manner as are conventional PTFE vascular grafts. Moreover, the dual porosity graft enhances tissue ingrowth.

Vascular grafts or tubes of various inner and outer surface properties may have advantages over standard PTFE grafts in situations where a higher porosity surface is desired. It is important to be able to provide this high porosity surface without significantly affecting the other physical properties of the graft. A graft having a higher inner porosity may be beneficial for accelerated healing of an implanted vascular graft, whereas a graft having a higher outside porosity may be beneficial in the case of a blood access affliction because the increased porosity accelerates tissue incorporation and allows for an earlier use of the graft in blood access procedures.

Dual porosity tubes of the present invention are not limited to use as vascular grafts. Such tubes can also be used in filtration, gas-liquid separations, and as barriers for bacterial contamination.

While the invention has been described with reference to preferred embodiments thereof, the description is for illustrative purposes only and is not to be construed as limiting the scope of the invention. Various modifications and changes may be made by those skilled in the art without departing from the true spirit of the scope of the invention as defined by the appended claims.

We claim:

1. A method of producing a dual porosity PTFE tube, said method comprising the steps of:

a. preforming a first inner tubular billet of PTFE resin particles having an average particle size of less than or equal to 355μ and a lubricant, the first tubular billet having a predetermined lube level in the range of 50 to 150 grams of lubricant to 500 grams PTFE resin;

b. preforming a second outer tubular billet of PTFE resin particles having an average particle size of greater than or equal to 450μ and a lubricant, the second tubular billet having a lube level in the range of 50 to 150 grams of lubricant to 500 grams PTFE resin and different from the predetermined lube level in the first inner tubular billet;

c. concentrically joining the first inner and the second outer tubular billets thereby forming a tubular extrusion billet;

d. co-extruding the tubular extrusion billet into a composite tubular extrudate;

e. longitudinally expanding the extrudate, thereby providing a PTFE tube having an inner surface with a first porosity and an outer surface with a second porosity different from the first porosity; and f. sintering the extrudate.

2. The method of claim 1, wherein the dual porosity graft produced thereby has an average inner surface internodal distance greater than 8μ and average outer surface internodal distance greater than 55μ.

3. The method of claim 2, wherein the dual porosity graft produced thereby has an average inner surface internodal distance in the range of 8 to 40μ and an average outer surface internodal distance in the range of 55 to 150μ.

4. The method of claim 1, wherein the dual porosity graft produced thereby has an average outer surface internodal distance greater than 8μ and average inner surface internodal distance greater than 55μ.

5. The method of claim 4, wherein the dual porosity graft produced thereby has an average inner surface internodal distance in the range of 8 to 40μ and an average outer surface internodal distance in the range of 55 to 150μ.

* * * * *

UNITED STATES PATENT AND TRADEMARK OFFICE
CERTIFICATE OF CORRECTION

PATENT NO. : 5,453,235
DATED : September 26, 1995
INVENTOR(S) : Calcote, et. al.

It is certified that error appears in the above-indentified patent and that said Letters Patent is hereby corrected as shown below:

Title page, item [54] in the Title, delete the "FTFE", and insert --PTFE-- therefore.

Column 1, line 2, delete "FTFE", and insert --PTFE-- therefore.

Signed and Sealed this

Twelfth Day of March, 1996

Attest:

BRUCE LEHMAN

Attesting Officer

Commissioner of Patents and Trademarks